United States Patent [19]

Nagel

[11] 4,064,143

[45] Dec. 20, 1977

[54] OLEANDOMYCIN DERIVATIVES

[75] Inventor: Arthur A. Nagel, Gales Ferry, Conn.

[73] Assignee: Pfizer Inc., New York, N.Y.

[21] Appl. No.: 749,481

[22] Filed: Dec. 10, 1976

[51] Int. Cl.$^2$ ............................................. C07D 315/00
[52] U.S. Cl. ..................................... 260/343; 424/279
[58] Field of Search .......................................... 260/343

[56] References Cited

U.S. PATENT DOCUMENTS 3,144,466  8/1964  Celmer .................................. 260/343

*Primary Examiner*—Norma S. Milestone
*Attorney, Agent, or Firm*—Francis X. Murphy; Charles J. Knuth; Albert E. Frost

[57] ABSTRACT

Certain derivatives of the macrolide antibiotic oleandomycin, in which the L-oleandrosyl residue has been replaced by a 2-substituted-3-methoxytetrahydrofuran-5-yl moiety. The compounds of the invention are useful as antibacterial agents.

16 Claims, No Drawings

OLEANDOMYCIN DERIVATIVES

BACKGROUND OF THE INVENTION

This invention relates to certain new chemical compounds, which have useful antibacterial properties and which are new members of the class of antibiotics known as the macrolides. More particularly the new chemical compounds of the present invention are derivatives of the well-known antibiotic oleandomycin, in which the L-oleandrosyl unit has been replaced by a substituted tetrahydrofuranyl moiety.

Oleandomycin derivatives in which the L-oleandrosyl unit has been replaced by a hydrogen atom have been reported in U.S. Pat. No. 3,144,466. However, oleandomycin derivatives in which the L-oleandrosyl unit has been replaced by other heterocyclic groups have not been reported previously in the prior art.

SUMMARY OF THE INVENTION

It is the principal object of this invention to provide novel compounds of the formula

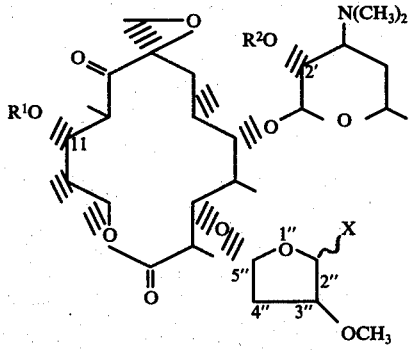

and the pharmaceutically-acceptable acid-addition salts thereof;
wherein $R^1$ and $R^2$ are each selected from the group consisting of hydrogen and lower-alkanoyl, and X is selected from the group consisting of vinyl, ethyl and formyl;
said compounds being of value as antibacterial agents, particularly for use in mammals, especially humans.

Throughout this specification, the term "lower-alkanoyl" is intended to include those groups having from 2 to 5 carbon atoms. However, the preferred alkanoyl groups for $R^1$ and $R^2$ are acetyl and propionyl.

A second object of this invention is to provide a process for the preparation of the compounds of the formula I, wherein $R^1$ and $R^2$ are each selected from the group consisting of hydrogen and lower-alkanoyl and X is vinyl. Said process comprises a ring-contraction reaction using a 4"-O-(N-[alkoxycarbonyl]sulfamoyl) derivative of oleandomycin.

DETAILED DESCRIPTION OF THE INVENTION

In one method according to the invention, the compounds of the formula I, wherein $R^1$ and $R^2$ are each selected from the group consisting of hydrogen and lower-alkanoyl and X is vinyl, are prepared from the corresponding compound of the formula

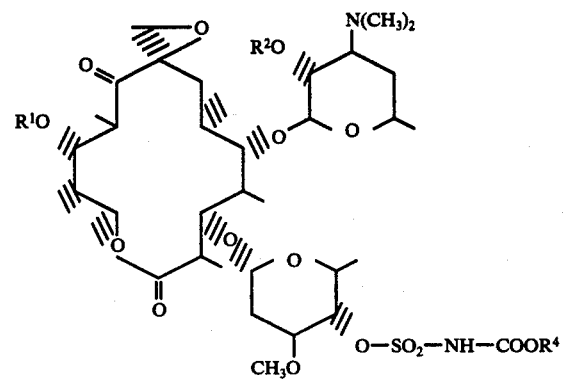

wherein $R^1$ and $R^2$ are each selected from the group consisting of hydrogen and lower-alkanoyl and $R^4$ is alkyl having from one to 5 carbon atoms. Preferred alkyl groups for $R^4$ are methyl and ethyl. This conversion is normally carried out by heating the said compound of the formula II in a dry, hydrocarbon solvent, at a temperature in the range from about 130° C. to about 160° C. until the reaction is substantially complete. The reaction normally takes a few hours substantially to reach completion; for example at about 140° C. a reaction time of about 1 to 2 hours is typically used. A convenient way of carrying out this conversion involves heating the said compound of the formula II in refluxing xylene. Although this is not essential for the success of the reaction, is it sometimes advantageous to add a small volume of a low-boiling co-solvent, such as chloroform, to assist in rapid dissolution of the said compound of the formula II. The co-solvent is then removed by distillation during the early stages of the conversion. The product of the formula I can be recovered simply by evaporation at the end of the reaction.

The compounds of the formula I, wherein $R^1$ and $R^2$ are each selected from the group consisting of hydrogen and lower-alkanoyl and X is ethyl, are prepared by hydrogenation of the corresponding compound wherein X is vinyl. This is a conventional hydrogenation procedure, and it is usually carried out by stirring or shaking a solution of the compound of the formula I, wherein X is a vinyl group, under an atmosphere of hydrogen, or hydrogen mixed with an inert diluent such as nitrogen or argon, in the presence of a hydrogenation catalyst. Suitable solvents for this hydrogenation reaction are those which substantially dissolve the starting compound of the formula I, but which do not themselves suffer hydrogenation or hydrogenolysis. Examples of such solvents include ethers such as diethyl ether, tetrahydrofuran, dioxan, 1,2-dimethoxyethane; low molecular weight esters such as ethyl acetate and butyl acetate; tertiary amides such as N,N-dimethylformamide, N,N-dimethylacetamide and N-methylpyrrolidone, and mixtures thereof. Introduction of the hydrogen gas into the reaction medium is usually accomplished by carrying out the reaction in a sealed vessel, containing the compound of the formula I, the solvent, the catalyst and the hydrogen. The pressure inside the reaction vessel can vary from about 1 atmosphere to about 100 atmospheres. The preferred pressure range, when the atmosphere inside the reaction vessel is substantially pure hydrogen, is from about 2 atmospheres to about 5 atmospheres. The hydrogenation is generally run at a temperature of from about 0° to about 100° C., and preferably from about 25° to about 50° C. Utilizing the preferred temperature and pressure values, hydrogenation generally takes place in a few hours, e.g., from about 2 hours to about 20 hours. The catalysts used in this hydrogenation reaction are the type of agents known in the art for this kind of transformation. However, a preferred agent is palladium, which can be used as the pure metal or suspended on an inert support such as carbon. The palladium is usually present in an amount from about 0.1 to about 100 mol. percent, based on the compound of the formula I. The preferred amount is greater than about 10 mol. percent.

The final product of the formula I, wherein X is ethyl, can be recovered by standard procedures. For example, it is common simply to remove the catalyst by filtration and then remove the solvent by evaporation, leaving the crude product. The latter crude product can be used as such or it can be purified by such well-known techniques as recrystallization and chromatography.

The compounds of the formula I, wherein $R^1$ and $R^2$ are each selected from the group consisting of hydrogen and lower-alkanoyl and X is formyl, are obtained by oxidative cleavage of the vinyl group of the corresponding compound of the formula I, wherein X is vinyl. Although a variety of reagents known in the art for this purpose can be used, a particularly convenient method involves treatment of the vinyl compound with osmium tetroxide followed by an alkali metal periodate, such as sodium or potassium periodate. In a typical procedure, the vinyl compound is dissolved in aqueous tetrahydrofuran and treated with a catalytic amount of osmium tetroxide at about 25° C. After the osmate ester has formed, the reaction mixture is treated with an excess (e.g. about 5 molar equivalents) of sodium periodate. Oxidation is complete within a few hours at about 25° C., and then the product is isolated by standard procedures.

The compounds of the formula I, wherein $R^1$ is selected from the group consisting of hydrogen and lower-alkanoyl, $R^2$ is hydrogen and X is selected from the group consisting of vinyl, ethyl and formyl, can also be prepared from the corresponding compound, wherein $R^2$ is lower-alkanoyl, by solvolytic removal of the alkanoyl group at C-2'. This is readily carried out by treating the appropriate compound of the formula I, wherein $R^2$ is lower-alkanoyl, with a water-miscible primary alkanol having from 1 to 4 carbon atoms (preferably methanol) at a temperature in the range from about 15° C. to about 45° C. for about 24 hours to about 3 weeks. In general, sufficient alkanol to dissolve the said compound of the formula I, wherein $R^2$ is alkanoyl, is normally used. At the end of the reaction, the product is usually isolated simply by solvent evaporation.

The starting materials of the formula II, wherein $R^1$ is selected from the group consisting of hydrogen and lower-alkanoyl, $R^2$ is lower-alkanoyl and $R^4$ lower-alkyl are prepared by reaction of the corresponding oleandomycin derivative of the formula

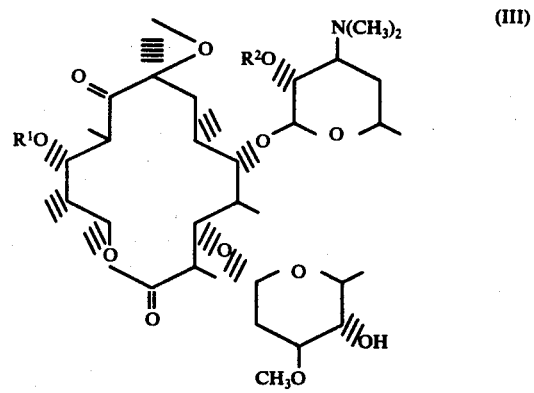

with the required alkyl (carboxysulfamoyl)triethylammonium hydroxide inner salt of the formula

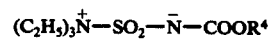

The reaction is usually carried out by contacting the compound of the formula III with about a four-fold excess of the compound of the formula IV, in a reaction-inert organic solvent, such as benzene. The reaction is normally conducted at or about 25° C., and it usually takes about 20 hours to reach completion. After removal of impurities by filtration, the compound of the formula II is recovered by evaporation of the solvent.

The starting materials of the formula II, wherein $R^1$ is selected from the group consisting of hydrogen and lower-alkanoyl, $R^2$ is hydrogen and $R^4$ is lower-alkyl, are prepared from the corresponding compound wherein $R^2$ is lower-alkanoyl, by solvolytic removal of the lower-alkanoyl group from C-2'. This is carried by the method described before for removal of the lower-alkanoyl group from C-2' in a compound of the formula I, wherein $R^1$ is selected from the group consisting of hydrogen and lower-alkanoyl, $R^2$ is lower-alkanoyl and X is selected from the group consisting of vinyl, ethyl and formyl.

The oleandomycin derivatives of the formula III are either known compounds, which are prepared by the published procedures, or they are homologues of known compounds, which are prepared by analogous procedures. See, for example, U.S. Pat. Nos. 3,022,219 and 3,144,466.

The alkyl (carboxysulfamoyl)triethylammonium hydroxide inner salts of the formula IV are prepared by reaction of chlorosulfonyl isocyanate and the appropriate alcohol of the formula $R^4OH$ in the presence of triethylamine, according to standard procedures.

The compounds of formula I, wherein $R^1$, $R^2$ and X are as defined previously, form acid-addition salts, and all such acid-addition salts are to be considered within the scope and purview of this invention. The salts are prepared by well-known methods, such as, for example, by combining a solution of the compound of the formula I in a suitable solvent (e.g. ether or acetone) with a solution containing one molar equivalent of the appropriate acid. If the salt precipitates, it is recovered by filtration; alternatively, it can be recovered by evaporation of the solvent. Although, when contemplating therapeutic use for a compound of the instant invention it is necessary to use a pharmaceutically-acceptable salt, salts other than these can be used for a variety of other purposes. Such purposes include isolating and purifying particular compounds, and interconverting pharmaceutically-acceptable salts with their non-salt counterparts. Of particular value are the sulfate, hydrochloride, hydrobromide, nitrate, phosphate, citrate, tartrate, pamoate, amsonate, perchlorate, sulfosalicylate, p-toluenesulfonate, aspartate and lauryl sulfate salts.

The oleandomycin derivatives of the formula I described herein exhibit in vitro activity against a variety of gram-positive microorganisms, e.g. *Straphylococcus aureus* and *Streptococcus pyrogenes,* and against certain gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like, for sterilization purposes, e.g., sick-room utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media, that is, media which have no harmful effect on the active ingredient. For such purposes, it will generally be acceptable to employ concentrations of active ingredients of from about 0.01 percent to about 10 percent by weight based on total composition.

Additionally, the compounds of this invention of the formula I are active versus gram-positive and certain gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the LD$_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated four, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 1 mg./kg. to about 200 mg./kg. of body weight. The favored dosage range is from about 5 mg./kg. to about 100 mg./kg. of body weight and the preferred range from about 5 mg./kg. to about 50 mg./kg. of body weight. Vehicles suitable for parenteral injection may be either aqueous such as water, isotonic saline, isotonic dextrose, Ringer's solution, or non-aqueous such as fatty oils of vegetable origin (cotten seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc., buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the Examples presented herein, no effort was made to recover the maximum amount of product produced or to optimize the yield of a given product. The Examples are merely illustrative of the process and of the products obtainable thereby.

EXAMPLE I 11,2'-Di-O-Acetyl-4''-O-(N-[methoxycarbonyl]sulfamoyl)oleandomycin To a solution of 11.5 g (14.9 mmole) of 11,2'-di-O-acetyloleandomycin in 100 ml. of dry benzene was added 10.6 g. (44.7 mmole) of methyl (carboxysulfamoyl)triethylammonium hydroxide inner salt, in portions, over a few minutes. The reaction mixture was stirred for 20 hours at 25° C. and then it was filtered. The filtrate was added slowly to 600 ml. of ether with rapid stirring. The solid which precipitated was removed by filtration and recrystallized from chloroform-ether. This afforded 12.0 g. of the title compound.

The IR spectrum of the product (KBr disc) showed absorptions at 3450, 2940, 1740, 1660, 1615, 1460, 1370, 1280, 1230, 1160, 1105, 1040, 890, 865, 770 and 745 cm.$^{-1}$.

EXAMPLE II

The procedure of Example I is repeated, and the oleandomycin derivatives used therein is:

2'-O-acetyloleandomycin,
2'-O-propionyloleandomycin,
11-O-acetyloleandomycin,
11,2'-di-O-acetyloleandomycin,
11,2'-di-O-acetyloleandomycin,
11,2'-di-O-propionyloleandomycin and
11-O-propionyl-2'-O-acetyloleandomycin, respectively, and the alkyl (carboxysulfamoyl)triethylammonium hydroxide inner salt is:

methyl (carboxysulfamoyl)treithylammonium hydroxide inner salt,
n-pentyl (carboxysulfamoyl)triethylammonium hydroxide inner salt,
ethyl (carboxysulfamoyl)triethylammonium hydroxide inner salt,
ethyl (carboxysulfamoyl)triethylammonium hydroxide inner salt,
isopropyl (carboxysulfamoyl)triethylammonium hydroxide inner salt, methyl (carboxysulfamoyl)triethylammonium hydroxide inner salt and ethyl (carboxysulfamoyl)triethylammonium hydroxide inner salt, respectively. This affords the following compounds:

2'-O-acetyl-4''-O-(N-[methoxycarbonyl]sulfamoyl)oleandomycin,
2'-O-propionyl-4''-O-(N-[n-pentyloxycarbonyl]sulfamoyl)oleandomycin,
11-O-acetyl-4''-O-(N-[ethoxycarbonyl]sulfamoyl)oleandomycin,
11,2'-di-O-acetyl-4''-O-(N-[ethoxycarbonyl]sulfamoyl)oleandomycin,
11,2'-di-O-acetyl-4''-O-(N-[isopropoxycarbonyl]sulfamoyl)oleandomycin,
11,2'-di-O-propionyl-4''-O-(N-[methoxycarbonyl]sulfamoyl)oleandomycin and
11-O-propionyl-2'-O-acetyl-4''-O-(N-[ethoxycarbonyl]sulfamoyl)oleandomycin respectively.

EXAMPLE III 11,2'-Di-O-acetyl-3-des(oleandrosyloxy)-3-(2''-vinyl-3''-methoxytetrahydrofuran-5''-yloxy)oleandomycin A mixture of 10.0 g. (10.8 mmole) of 11,2'-di-O-acetyl-4''-O-(N-[methoxycarbonyl]sulfamoyl)oleandomycin, 160 ml. of dry chloroform and 400 ml. of dry xylene was heated to reflux. The reaction mixture was maintained at reflux for 1.5 hours, while being attached to a Dean-Stark trap. At this point, the hot supernatant solvent was removed by decantation and allowed to cool. The solid which precipitated was removed by filtration and discarded, and then the filtrate was evaporated in vacuo. This afforded 5.5 g. of crude product as a yellow foam. The crude product was purified by chromatography using silica gel as the absorbent and a 1:1 mixture of chloroform-acetone as the eluent. The yield of purified product was 1.0 g. (12% yield).

EXAMPLE IV

The procedure of Example III is repeated, except that the 11,2'-di-O-acetyl-4''-O-(N-[methoxycarbonyl]sulfamoyl)oleandomycin is replaced by:

2'-O-acetyl-4''-o-(N-[methoxycarbonyl]sulfamoyl)oleandomycin,
2'-O-propionyl-4''-O-(N-[n-pentyloxycarbonyl]sulfamoyl)oleandomycin,
11-O-acetyl-4''-O-(N-[ethoxycarbonyl]sulfamoyl)oleandomycin,
11,2'-di-O-acetyl-4''-O-(N-[ethoxycarbonyl]sulfamoyl)oleandomycin,
11,2'-di-O-acetyl-4''-O-(N-[isopropoxycarbonyl]sulfamoyl)oleandomycin,
11,2'-di-O-propionyl-4''-O-(N-[methoxycarbonyl]sulfamoyl)oleandomycin and
11-O-propionyl-2'-O-acetyl-4''-O-(N-[ethoxycarbonyl]sulfamoyl)oleandomycin, respectively. This affords the following compounds:

2'-O-acetyl-3-des(oleandrosyloxy)-3-(2''-vinyl-3''-methoxytetrahydrofuran-5''-yloxy)oleandomycin,
2'-O-propionyl-3-des(oleandrosyloxy)-3-(2''-vinyl-3''-methoxytetrahydrofuran-5''-yloxy)oleandomycin,
11-O-acetyl-3-des(oleandrosyloxy)-3-(2''-vinyl-3''-methoxytetrahydrofuran-5-yloxy)oleandomycin,
11,2'-di-O-acetyl-3-des(oleandrosyloxy)-3-(2''-vinyl-3''-methoxytetrahydrofuran-5''-yloxy)oleandomycin,
11,2'-di-O-acetyl-3-des(oleandrosyloxy)-3-(2''-vinyl-3''-methoxytetrahydrofuran-5-yloxy)oleandomycin,
11,2'-di-O-propionyl-3-des(oleandrosyloxy)-3-(2''-vinyl-3''-methoxytetrahydrofuran-5-yloxy)oleandomycin and
11-O-propionyl-2'-O-acetyl-3-des(oleandrosyloxy)-3-(2''-vinyl-3''-methoxytetrahydrofuran-5''-yloxy)oleandomycin, respectively.

EXAMPLE V

11-O-Acetyl-3-des(oleandrosyloxy)-3-(2''-vinyl-3''-methoxytetrahydrofuran-5''-yloxy)oleandomycin A solution of 0.4 g. of 11,2'-di-O-acetyl-3-des(oleandrosyloxy)-3-(2''-vinyl-3''-methoxytetrahydrofuran-5''-yloxy)oleandomycin in a small volume of methanol was stored at ambient temperature for 3 days and then the solvent was removed by evaporation in vacuo. This afforded a quantitative yield of 11-O-acetyl-3-des(oleandrosyloxy)-3-(2''-vinyl-3''-methoxytetrahydrofuran-5''-yloxy)oleandomycin.

The IR spectrum of the product (KBr disc) showed absorptions at 3400, 2940, 1735, 1610, 1460, 1380, 1230, 1180, 1110, 1025 and 755 cm.$^{-1}$.

EXAMPLE VI

The following compounds are solvolysed, according to the procedure of Example V.

2'-O-acetyl-3-des(oleandrosyloxy)-3-(2''-vinyl-3''-methoxytetrahydrofuran-5''-yloxy)oleandomycin,
2'-O-propionyl-3-des(oleandrosyloxy)-3-(2''-vinyl-3''-methoxytetrahydrofuran-5''-yloxy)oleandomycin,
11,2'-di-O-acetyl-3-des(oleandrosyloxy)-3-(2''-vinyl-3''-methoxytetrahydrofuran-5''-yloxy)oleandomycin,
11,2'-di-O-acetyl-3-des(oleandrosyloxy)-3-(2''-vinyl-3''-methoxytetrahydrofuran-5-yloxy)oleandomycin,
11,2'-di-O-propionyl-3-des(oleandrosyloxy)-3-(2''-vinyl-3''-methoxytetrahydrofuran-5-yloxy)oleandomycin and
11-O-propionyl-2'-O-acetyl-3-des(oleandrosyloxy)-3-(2''-vinyl-3''-methoxytetrahydrofuran-5''-yloxy)oleandomycin, respectively. This affords:

3-des(oleandrosyloxy)-3-(2''-vinyl-3''-methoxytetrahydrofuran-5''-yloxy)oleandomycin,
3-des(oleandrosyloxy)-3-(2''-vinyl-3''-methoxytetrahydrofuran-5''-yloxy)oleandomycin,
11-O-acetyl-3-des(oleandrosyloxy)-3-(2''-vinyl-3''-methoxytetrahydrofuran-5''-yloxy)oleandomycin,
11-O-acetyl-3-des(oleandrosyloxy)-3-(2''-vinyl-3''-methoxytetrahydrofuran-5''-yloxy)oleandomycin,
11-O-propionyl-3-des(oleandrosyloxy)-3-(2''-vinyl-3''-methoxytetrahydrofuran-5''-yloxy)oleandomycin and
11O-propionyl-3-des(oleandrosyloxy)-3-(2''-vinyl-3''-methoxytetrahydrofuran-5''-yloxy)oleandomycin, respectively.

EXAMPLE VII 11,2'-Di-O-acetyl-3-des(oleandosyloxy)-3-(2"-ethyl-3"-methoxytetrahydrofuran-5"-yloxy)oleandomycin A mixture of 150 mg. of 11,2'-di-O-acetyl-3-des-(oleandrosyloxy)-3-(2"-vinyl-3"-methoxytetrahydrofuran-5"-yloxy)oleandomycin, 150 mg. of 10% palladium-on-carbon and 20 ml. of ethyl acetate is shaken under an atmosphere of hydrogen, at 25° C., and at an initial pressure 50 psig. After 18 hours, the reaction mixture was filtered and the residue discarded. The filtrate was evaporated in vacuo, giving 140 mg. of the title product as an oil.

The above product was combined with a further quantity of equivalent material from a similar experiment. The combined material was purified by column chromatography on silica gel using a 2:1 mixture of chloroformacetone as eluent.

The IR spectrum (KBr disc) of the purified product showed absorptions at 3400, 2900, 1740, 1600, 1460, 1200 and 1060 cm.$^{-1}$.

EXAMPLE VIII

The products of Example IV are hydrogenated according to the procedure of Example VII. This affords:

2'-O-acetyl-3-des(oleandrosyloxy)-3-(2"-ethyl-3"-methoxytetrahydrofuran-5"-yloxy)oleandomycin,
2'-O-propionyl-3-des(oleandrosyloxy)-3-(2"-ethyl-3"-methoxytetrahydrofuran-5"-yloxy)oleandomycin,
11-O-acetyl-3-des(oleandrosyloxy)-3-(2"-ethyl-3"-methoxytetrahydrofuran-5-yloxy)oleandomycin,
11,2'-di-O-acetyl-3-des(oleandrosyloxy)-3-(2"-ethyl-3"-methoxytetrahydrofuran-5"-yloxy)oleandomycin,
11,2'-di-O-acetyl-3-des(oleandrosyloxy)-3-(2"-ethyl-3"-methoxytetrahydrofuran-5"-yloxy)oleandomycin,
11,2'-di-O-propionyl-3-des(oleandrosyloxy)-3-(2"-ethyl-3"-methoxytetrahydrofuran-5-yloxy)oleandomycin and
11-O-propionyl-2'-O-acetyl-3-des(oleandrosyloxy)-3-(2"-ethyl-3"-methoxytetrahydrofuran-5"-yloxy)oleandomycin), respectively.

EXAMPLE IX

The following compounds are solvolysed according to the procedure of Example V:

2'-O-acetyl-3-des(oleandrosyloxy)-3-(2"-ethyl-3"-methoxytetrahydrofuran-5"-yloxy)oleandomycin,
2'-O-propionyl-3-des(oleandrosyloxy)-3-(2"-ethyl-3"-methoxytetrahydrofuran-5"-yloxy)oleandomycin,
11,2'-di-O-acetyl-3-des(oleandrosyloxy)-3-(2"-ethyl-3"-methoxytetrahydrofuran-5"-yloxy)oleandomycin,
11,2'-di-O-acetyl-3-des(oleandrosyloxy)-3-(2"-ethyl-3"-methoxytetrahydrofuran-5-yloxy)oleandomycin,
11,2'-di-O-propionyl-3-des(oleandrosyloxy)-3-(2"-ethyl-3"-methoxytetrahydrofuran-5-yloxy)oleandomycin and
11-O-propionyl-2'-O-acetyl-3-des(oleandrosyloxy)-3-(2"-ethyl-3"-methoxytetrahydrofuran-5"-yloxy)oleandomycin), respectively. This affords:

3-des(oleandrosyloxy)-3-(2"'-ethyl-3"-methoxytetrahydrofuran-5"-yloxy)oleandomycin,
3-des(oleandrosyloxy)-3-(2"-ethyl-3"-methoxytetrahydrofuran-5"-yloxy)oleandofuran-5"-yloxy)oleandomycin,
11-O-acetyl-3-des(oleandrosyloxy)-3-(2"-ethyl-3"-methoxytetrahydrofuran-5"-yloxy)oleandomycin,
11-O-acetyl-3-des(oleandrosyloxy)-3-(2"-ethyl-3"-methoxytetrahydrofuran-5"-yloxy)oleandomycin,
11-O-propionyl-3-des(oleandrosyloxy)-3-(2"-ethyl-3"-methoxytetrahydrofuran-5"-yloxy)oleandomycin and
11-O-propionyl-3-des(oleandosyloxy)-3-(2"-ethyl-3"-methoxytetrahydrofuran-5"-yloxy)oleandomycin, respectively.

EXAMPLE X 11,2-Di-O-acetyl-3-des(oleandrosyloxy)-3-(2"-formyl-3"-methoxytetrahydrofuran-5"-yloxy)oleandomycin A solution to 0.2 g. of 11,2'-di-O-acetyl-3-des(oleandrosyloxy)-3-(2"-vinyl-3"-methoxytetrahydrofuran-5"-yloxy)oleandomycin in 10 ml. of 9:1 tetrahydrofuran-water was prepared and the pH was adjusted to 6.0 using 1N hyrochloric acid. To this solution was added 7 ml. of a 1% solution of osmium tetraxide in ether, at 25° C., and the mixture was stirred for 20 minutes. At this point, 0.286 g. of sodium periodate was added and stirring was continued for 60 minutes. To the reaction mixture was then added 50 ml. of ethyl acetate and 50 ml. of 1M sodium bisulfite. Stirring was continued. for 40 minutes during which time the pH rose to 9.5.

The organic phase was removed and washed successively with water and saturated sodium chloride solution. The solution was then dried, and evaporated in vacuo, leaving 170 mg. of the title compound as a clear oil. The product was purified by column chromatography using silica gel as absorbent and eluting with 2:1 acetone-chloroform. Fractions 60 to 80 were combined and evaporated giving 14 mg. of the title compound. The IR spectrum (KBr disc) showed absorptions at 3390, 2890, 1735, 1590, 1460, 1380, 1230 and 1050 cm.$^{-1}$.

EXAMPLE XI

Oxidation of the products of Example IV, using osmium tetroxide and sodium periodate, according to the procedure of Example X, leads to the following products:

2'-O-acetyl-3-des(oleandrosyloxy)-3-(2"-formyl-3"-methoxytetrahydrofuran-5"-yloxy)oleandomycin,
2'-O-propionyl-3-des(oleandrosyloxy)-3-(2"-formyl-3"-methoxytetrahydrofuran-5"-yloxy)oleandomycin,
11-O-acetyl-3-des(oleandrosyloxy)-3-(2"-formyl-3"-methoxytetrahydrofuran-5-yloxy)oleandomycin,
11,2'-di-O-acetyl-3-des(oleandrosyloxy)-3-(2"-formyl-3"-methoxytetrahydrofuran-5"-yloxy)oleandomycin,
11,2'-di-O-acetyl-3-des(oleandrosyloxy)-3-(2"-formyl-3"-methoxytetrahydrofuran-5-yloxy)oleandomycin,
11,2'-di-O-propionyl-3-des(oleandrosyloxy)-3-(2"-formyl-3"-methoxytetrahydrofuran-5-yloxy)oleanodomycin,
11,2'-di-O-propionyl-3-des(oleandrosyloxy)-3-(2"-formyl-3"-methoxytetrahydrofuran-5-yloxy)oleandomycin and 11-O-propionyl-2'-O-acetyl-3-des(oleandrosyloxy)-3-(2''-formyl-3''-methoxytetrahydrofuran-5''-yloxy)oleandomycin, respectively.

EXAMPLE XII

The following compounds are solvolysed in methanol, according to the procedure of Example V:

2'-O-acetyl- 3-des(oleandrosyloxy)-3-(2''-formyl-3''-methoxytetrahydrofuran-5''-yloxy)oleandomycin,
2'-O-propionyl-3-des(oleandrosyloxy)-3-(2''-formyl-3''-methoxytetrahydrofuran-5''-yloxy)oleandomycin,
11,2'-di-O-acetyl-3-des(oleandrosyloxy)-3-(2''-formyl-3''-methoxytetrahydrofuran-5''-yloxy)oleandomycin,
11,2'-di-O-acetyl-3-des(oleandrosyloxy)-3-(2''-formyl-3''-methoxytetrahydrofuran-5-yloxy)oleandomycin,
11,2'-di-O-propionyl-3des(oleandrosyloxy)-3-(2''-formyl-3''-methoxytetrahydrofuran-5-yloxy)oleandomycin and
11-O-propionyl-2'-O-acetyl-3-des(oleandrosyloxy)-3-(2''-formyl-3''-methoxytetrahydrofuran-5''-yloxy)oleandomycin, respectively. This affords:

3-des(oleandrosyloxy)-3-(2''-formyl-3''-methoxytetrahydrofuran-5''-yloxy)oleandomycin,
3-des(oleandrosyloxy)-3-(2''-formyl-3''-methoxytetrahydrofuran-5''-yloxy)oleandomycin,
11-O-acetyl-3-des(oleandrosyloxy)-3-(2''-formyl-3''-methoxytethrahydrofuran-5''-yloxy)oleandomycin,
11-O-acetyl-3-des(oleandrosyloxy)-3-(2''-formyl-3''-methoxytetrahydrofuran-5''-yloxy)oleandomycin,
11-O-propionyl-3-des(oleandrosyloxy)-3-(2''-formyl-3''-methoxytetrahydrofuran-5''-yloxy)oleandomycin and
11-O-propionyl-3-des(oleandosyloxy)-3-(2''-formyl-3''-methoxytetrahydrofuran-5''-yloxy)oleandomycin, respectively.

What is claimed is:

1. A compound of the formula:

and the pharmaceutically-acceptable acid-addition salts thereof;
  wherein $R^1$ and $R^2$ are each selected from the group consisting of hydrogen, acetyl and propionyl;
  and X is selected from the group consisting of vinyl, ethyl and formyl.

2. A compound according to claim 1, wherein $R^1$ is selected from the group consisting of acetyl and propionyl.

3. A compound according to claim 2, wherein $R^2$ is hydrogen.

4. A compound according to claim 2, wherein $R^2$ is acetyl.

5. A compound according to claim 4, wherein $R^1$ is acetyl.

6. The compound according to claim 5, wherein X is vinyl.

7. The compound according to claim 5, wherein X is ethyl.

8. The compound according to claim 5, wherein X is formyl.

9. A compound of the formula:

wherein
  $R^1$ and $R^2$ are each selected from the group consisting of hydrogen, acetyl and propionyl;
  and $R^4$ is alkyl having from one to five carbon atoms.

10. A compound according to claim 9, wherein $R^1$ is selected from the group consisting of acetyl and propionyl.

11. A compound according to claim 10, wherein $R^1$ and $R^2$ are each acetyl.

12. The compound according to claim 11, wherein $R^4$ is methyl.

13. A process for the preparation of a compound of the formula which comprises heating a compound of the formula

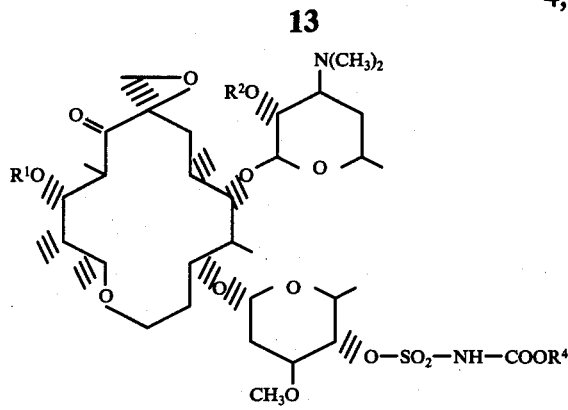

in a dry, hydrocarbon solvent, at a temperature in the range from about 130° C. to about 160° C;
  wherein $R^1$ and $R^2$ are each selected from the group consisting of hydrogen, acetyl and propionyl and $R^4$ is alkyl having from one to five carbon atoms.

14. The process according to claim 13, wherein the said hydrocarbon solvent is xylene.

15. The process according to claim 14, wherein $R^1$ and $R^2$ are each selected from the group consisting of acetyl and propionyl.

16. The process according to claim 14, wherein $R^1$ and $R^2$ are each acetyl and $R^4$ is methyl.

* * * * *

UNITED STATES PATENT OFFICE
CERTIFICATE OF CORRECTION

PATENT NO. : 4,064,143
DATED : December 20, 1977
INVENTOR(S) : Arthur A. Nagel, Gales Ferry, Conn.

It is certified that error appears in the above-identified patent and that said Letters Patent are hereby corrected as shown below:

Column 13, lines 10-13, that portion of the formula reading

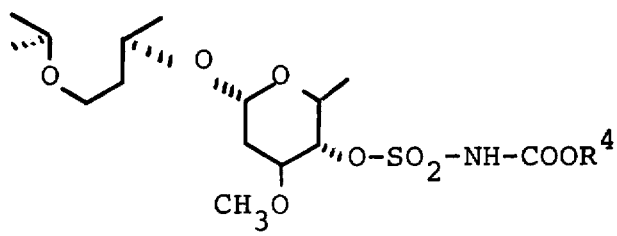

should read

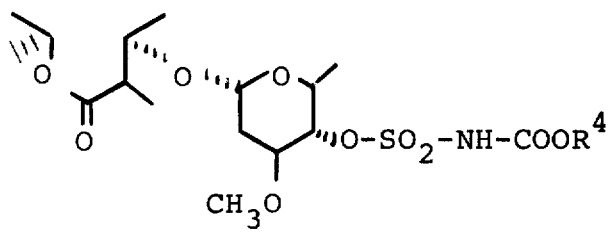

Signed and Sealed this

Eighth Day of August 1978

[SEAL]

Attest:

RUTH C. MASON
Attesting Officer

DONALD W. BANNER
Commissioner of Patents and Trademarks